(12) United States Patent
Yi et al.

(10) Patent No.: US 11,931,600 B2
(45) Date of Patent: Mar. 19, 2024

(54) SYSTEM AND METHOD FOR FORMING A TREATMENT PLAN FOR CHARGED PARTICLE THERAPY USING HYDROGEN DENSITY

(71) Applicant: University Of Maryland, Baltimore, Baltimore, MD (US)

(72) Inventors: Byong Yong Yi, Fulton, MD (US); Ulrich Langner, Upton, MA (US); Sina Mossahebi, Towson, MD (US); Chaitanya Kalavagunta, Ellicott City, MD (US)

(73) Assignee: University Of Maryland, Baltimore, Baltimore, MD (US)

( * ) Notice: Subject to any disclaimer, the term of this patent is extended or adjusted under 35 U.S.C. 154(b) by 818 days.

(21) Appl. No.: 16/979,419

(22) PCT Filed: Mar. 11, 2019

(86) PCT No.: PCT/US2019/021607
§ 371 (c)(1),
(2) Date: Sep. 9, 2020

(87) PCT Pub. No.: WO2019/173823
PCT Pub. Date: Sep. 12, 2019

(65) Prior Publication Data
US 2021/0361972 A1    Nov. 25, 2021

Related U.S. Application Data

(60) Provisional application No. 62/640,921, filed on Mar. 9, 2018.

(51) Int. Cl.
*G06T 7/11*  (2017.01)
*A61N 5/10*  (2006.01)

(52) U.S. Cl.
CPC ......... *A61N 5/1039* (2013.01); *A61N 5/1031* (2013.01); *A61N 5/1043* (2013.01);
(Continued)

(58) Field of Classification Search
CPC .. A61N 5/1039; A61N 5/1031; A61N 5/1043; A61N 5/1045; A61N 2005/1087;
(Continued)

(56) References Cited

U.S. PATENT DOCUMENTS

| 2014/0020044 A1 | 1/2014 | Ayres et al. |
| 2017/0025257 A1 | 1/2017 | Walde et al. |
| 2018/0099154 A1* | 4/2018 | Prieels ................. A61N 5/1064 |

OTHER PUBLICATIONS

Bar et al, "Experimental validation of DECT for proton therapy using heterogeneous tissue samples", Med. Phys., 45 (1), 2018.
(Continued)

*Primary Examiner* — David P Porta
*Assistant Examiner* — Fani Polyzos Boosalis
(74) *Attorney, Agent, or Firm* — Wolter Van Dyke Davis, PLLC; Eugene J. Molinelli; Cian O'Brien

(57) ABSTRACT

Techniques are presented for optimizing a treatment plan for charged particle therapy. The method includes obtaining medical image data voxels inside a subject in a reference frame of a radiation source that emits a beam of charged particles at multiple tracks with a controlled emitted energy at each track. Hydrogen density (HD) is determined based on the medical image data. Stopping power ratio (SPR) along a first beam having a first track and first emitted energy is calculated based on HD. A range to a Bragg peak is calculated along the first beam based on the SPR and the first emitted energy. The first beam track or the first emitted energy, or both, is modified based at least in part on the beam range to determine a second track and second emitted energy. Output data that indicates the second track and second emitted energy are sent.

9 Claims, 12 Drawing Sheets

(52) U.S. Cl.
CPC .............. *A61N 5/1045* (2013.01); *G06T 7/11* (2017.01); *A61N 2005/1087* (2013.01); *G06T 2207/10081* (2013.01); *G06T 2207/10088* (2013.01); *G06T 2207/30004* (2013.01)

(58) Field of Classification Search
CPC .............. G06T 7/11; G06T 2207/10081; G06T 2207/10088; G06T 2207/30004
See application file for complete search history.

(56) References Cited

OTHER PUBLICATIONS

Craft, et al, "Deliverable navigation for multicriteria step and shoot IMRT treatment planning", Phys Med Biol 2013; 58: 87-103.
Koivula et al, "Feasibility of MRI-only treatment planning for proton therapy in brain and prostate cancers: Dose calculation accuracy in substitute CT images", Med. Phys. 43 (8), 2016.
Li et al, "Comprehensive analysis of proton range uncertainties related to SPR estimation using dual energy CT imaging", Phys. Med. Biol. 62 7056, 2017.
Long, et al, "Sensitivity analysis for lexicographic ordering in radiation therapy treatment planning", Med Phys 2012; 39: 3445-55.
Mohler, et al, "Methodological accuracy of image-based electron density assessment using dual-energy computed tomography", Med. Phys. 44 (6), 2017.
Paganetti, "Range uncertainties in proton therapy and the role of Monte Carlo simulations", Phys Med Biol 2012; 57: R99-117.
Schneider, et al, "The calibration of CT Hounsfield units for radiotherapy treatment planning", Phys Med Biol 1996, 41 (1):111-24.
Sudhyadhom, "Determination of mean ionization potential using magnetic resonance imaging for the reduction of proton beam range uncertainties: theory and application", Phys. Med. Biol. 62 852, 2017.
Taasti et al, "Validation of proton stopping power ratio estimation based on dual energy CT using fresh tissue samples" Phys. Med. Biol 14;63(1):015012. 2017.
Van de Water, et al, "Improved efficiency of multi-criteria IMPT treatment planning using iterative resampling of randomly placed pencil beams", Phys Med Biol 2013; 58: 6969-83.
Wohlfahrt, et al, "Evaluation of Stopping-Power Prediction by Dual- and Single-Energy CT in an Anthropomorphic Ground-Truth Phantom", Int J Radiation Oncol Biol Phys, vol. 100, No. 1, pp. 244e253, 2018.
Vilches-Freixas, G. et al., "Comparison of projection- and image-based methods for proton stopping power estimation using dual energy CT," Physics and Imaging in Radiation Oncology (2017) vol. 3, p. 28-36.
Witt, M. et al., Optimization of the stopping-power-ratio to Hounsfield-value calibration curve in proton and heavy ion therapy, Zeitschrift fur Medizinische Physik, Dec. 2014, vol. 25, p. 251-263.
Yang, M. et al., Theoretical variance analysis of single- and dual-energy computed tomography methods for calculating proton stopping power ratios of biological tissues, • Physics in Medicine and Biology, Feb. 2010 (Feb. 2010) vol. 55(5), p. 1343-62.
International Search Report and Written Opinion for International Patent Application No. PCT/US19/21607 dated May 30, 2019, pp. 1-10.

\* cited by examiner

FIG. 3C
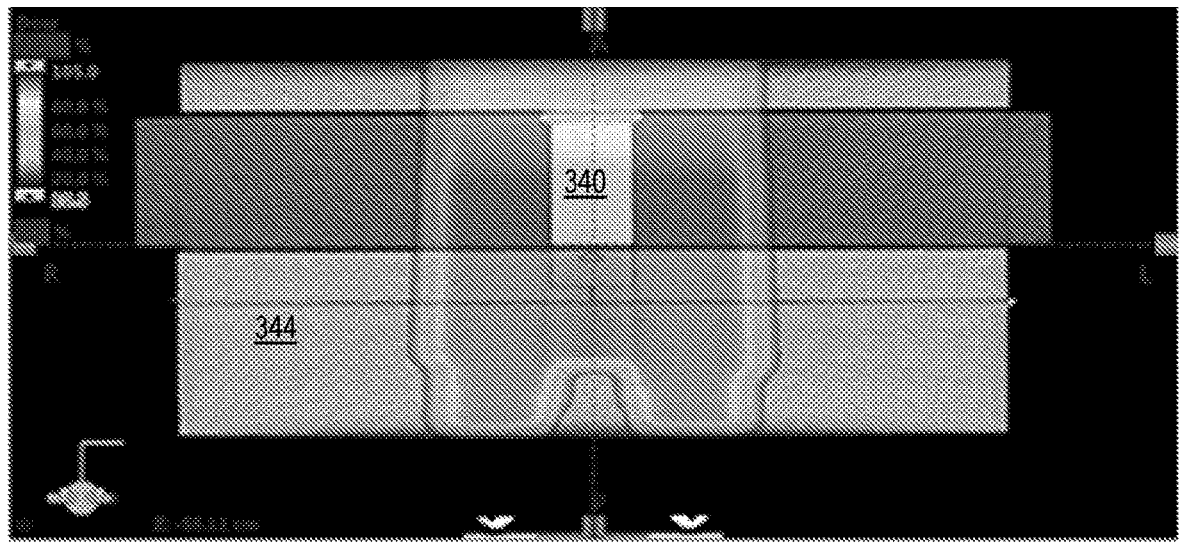
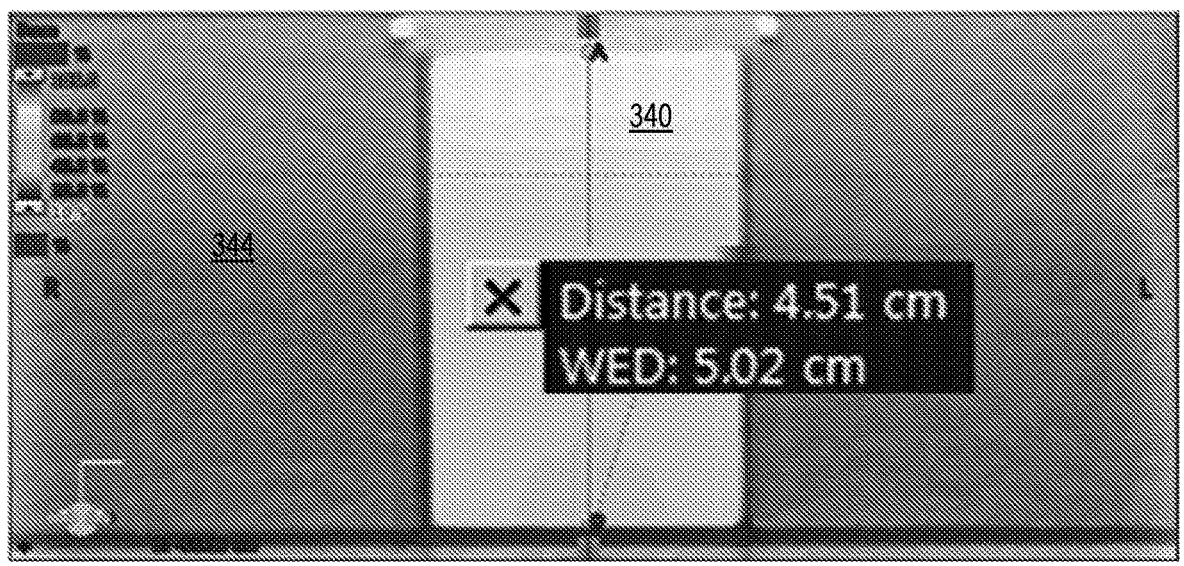
FIG. 3D

SYSTEM AND METHOD FOR FORMING A TREATMENT PLAN FOR CHARGED PARTICLE THERAPY USING HYDROGEN DENSITY

CROSS-REFERENCE TO RELATED APPLICATIONS

This application is a 371 national stage application of PCT Application No. PCT/US19/21607, filed Mar. 11, 2019, and claims benefit of Provisional Application No. 62/640,921, filed Mar. 9, 2018, under 35 U.S.C. § 119(e), the entire contents of which are hereby incorporated by reference as if fully set forth herein.

BACKGROUND

Radiotherapy is a treatment for cancer patients involving the use of high-energy radiation. When high-energy radiation is delivered to a subject, it kills cells in the body. Although the high-energy radiation kills tumor cells in the subject's body, it may also kill normal tissue cells and tissue cells of an organ-at-risk (OAR) that surround the tumor. Thus, the goal of conventional radiotherapy is to deliver a sufficient radiation dose to the tumor to kill the tumor cells while minimizing the radiation dose delivered to the normal tissue cells and OAR tissue cells that surround the tumor.

The use of charged particle therapy (such as proton therapy or Carbon ion therapy) for treating cancer has greatly increased over the past decade, mostly because of the advantageous interaction properties of charged particle beams. A charge particle beam initially deposits a relatively low dose upon entering the patient, and the deposited dose rises, as the average particle speed in the beam slows, to a sharp maximum deposited dose, known as the Bragg peak, near the end of the beam's range in the patient, ending in steep dose gradients at the distal edge of the Bragg peak. There is often little or no exiting radiation. The sharp Bragg peak and the finite range of the beam provide the ability to deliver a highly conformal treatment, allowing for dose escalation to the tumor and/or a reduction of exposure to the surrounding healthy tissues.

However, variations in particle beam absorption and stopping power (also called rate of energy loss) among different tissues, both healthy tissue and tumors, lead to uncertainties in the exact position of the distal dose gradient of the Bragg peak within the patient. Because of uncertainties in the position of the distal falloff, standard proton treatment techniques include the use of large treatment volume expansions to ensure target coverage and to avoid any possible undershoot or overshoot of the beam into nearby critical structures. These large safety margins limit the ability to exploit the steep dose gradients at the distal edge of the Bragg peak, thus reducing the full clinical potential of proton, and other charged particle, radiation therapy.

Hounsfield units (HU) are a dimensionless unit universally used in computed tomography (CT) scanning to express CT numbers in a standardized and convenient form. Current practice is to determine a charged particle stopping power ratio (SPR) from CT images of a subject using an empirically derived (HU)-to-SPR calibration curve (or stoichiometric calibration). A fundamental limitation in this approach is that human tissues with different HU values can have similar SPR values, and vice versa. The uncertainties in range to the Bragg peak related to imprecise values of SPR for a subject are estimated to be about 3.5% for both proximal and distal end of the target volume for the purposes of treatment planning. A recent article by Paganetti cited uncertainties of 2.7%.

Dual Energy CT (DECT) uses two different X-ray energies (i.e., wavelengths) to enhance the soft tissue contrast. DECT can provide more information about the types of tissues the beam traverses and potentially reduce the SPR uncertainty. However, DECT is expensive and not commonly available. Also there is no indication that the soft tissue contrast provided is directly related to mechanisms of SPR changes.

SUMMARY

It is here recognized that improvements in radiation treatment planning for charged particle beams, such as protons and Carbon ions, can be achieved by accounting for variations in hydrogen density in tissues along a treatment beam track.

In a first set of embodiments, a method is provided for optimizing a treatment plan for charge particle beam therapy. The method includes obtaining medical image data of multiple voxels inside a subject in a reference frame of a radiation source that emits a beam of charged particles at multiple tracks with a controlled emitted energy at each track. The method also includes, for a first beam having a first track and first emitted energy, determining hydrogen density at each voxel along the first beam selected from the plurality of voxels based on the medical image data. The method further includes calculating automatically on a processor stopping power ratio along the first beam based on the hydrogen density at each voxel along the first beam selected from the plurality of voxels. Still further, the method includes calculating range to a Bragg peak along the first beam based on the stopping power ratio and the first emitted energy. Even further still, the method includes automatically on a processor modifying the first beam track or the first emitted energy of the first beam, or both, based at least in part on the range to the Bragg peak to determine a second track and second emitted energy of a modified beam. Yet further, the method includes causing the radiation source to be operated to deliver the modified beam by sending automatically from the processor output data that indicates the second track and second emitted energy of the modified beam.

In some embodiments of the first set, the medical image data is proton density data from a magnetic resonance imaging device; and, said determining hydrogen density is performed automatically on a processor.

In some other embodiments of the first set, the medical image data is X-ray absorption data from a computed tomography imaging device. Said determining hydrogen density includes segmenting the medical image data into a tissue type at each voxel based on absorption value at each voxel and location inside patient of each voxel for at least each voxel along the first beam. This can be done manually or automatically on a processor. In these embodiments, hydrogen density is determined automatically on a processor at each voxel based on tissue type at each voxel for at least each voxel along the first beam.

In still other embodiments of the first set, the medical image data is difference in X-ray absorption data from a dual energy computed tomography (DECT) imaging device. Said determining hydrogen density includes segmenting the medical image data automatically on a processor into a tissue type at each voxel based on difference value at each voxel for at least each voxel along the first beam. Hydrogen density is determined automatically on the processor at each voxel based on tissue type at each voxel for at least each voxel along the first beam.

In some embodiments of the first set, said calculating automatically on a processor stopping power ratio further includes calculating stopping power ratio as a polynomial function of the hydrogen density expressed as a percentage at each voxel along the first beam selected from the plurality of voxels. In some of these embodiments, the polynomial function is a linear function for which the stopping power ratio is equal to a constant multiplied by the hydrogen density expressed as a percentage in a percentage range from 0 percent to about 20 percent. In some of these embodiments, the linear function gives the stopping power ratio as 0.872 plus 1.238 multiplied by the hydrogen density expressed as a percentage.

In other sets of embodiments, a computer-readable medium, or system including the radiation source, is configured to perform one or more steps of one or more of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 3A through FIG. 3D are block diagrams that illustrate example measurement equipment used to determine a calibration curve for SPR dependence on hydrogen density, according to an embodiment;

DETAILED DESCRIPTION

A method and apparatus are described for optimizing a treatment plan for charged particle therapy using hydrogen density. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of optimizing treatment plans for proton therapy of tumors. However, the invention is not limited to this context. In other embodiments, other targets in other regions of a human or non-human subject are irradiated with the same or other charged particles, such as Carbon ions.

1. Overview

Figure 1A:
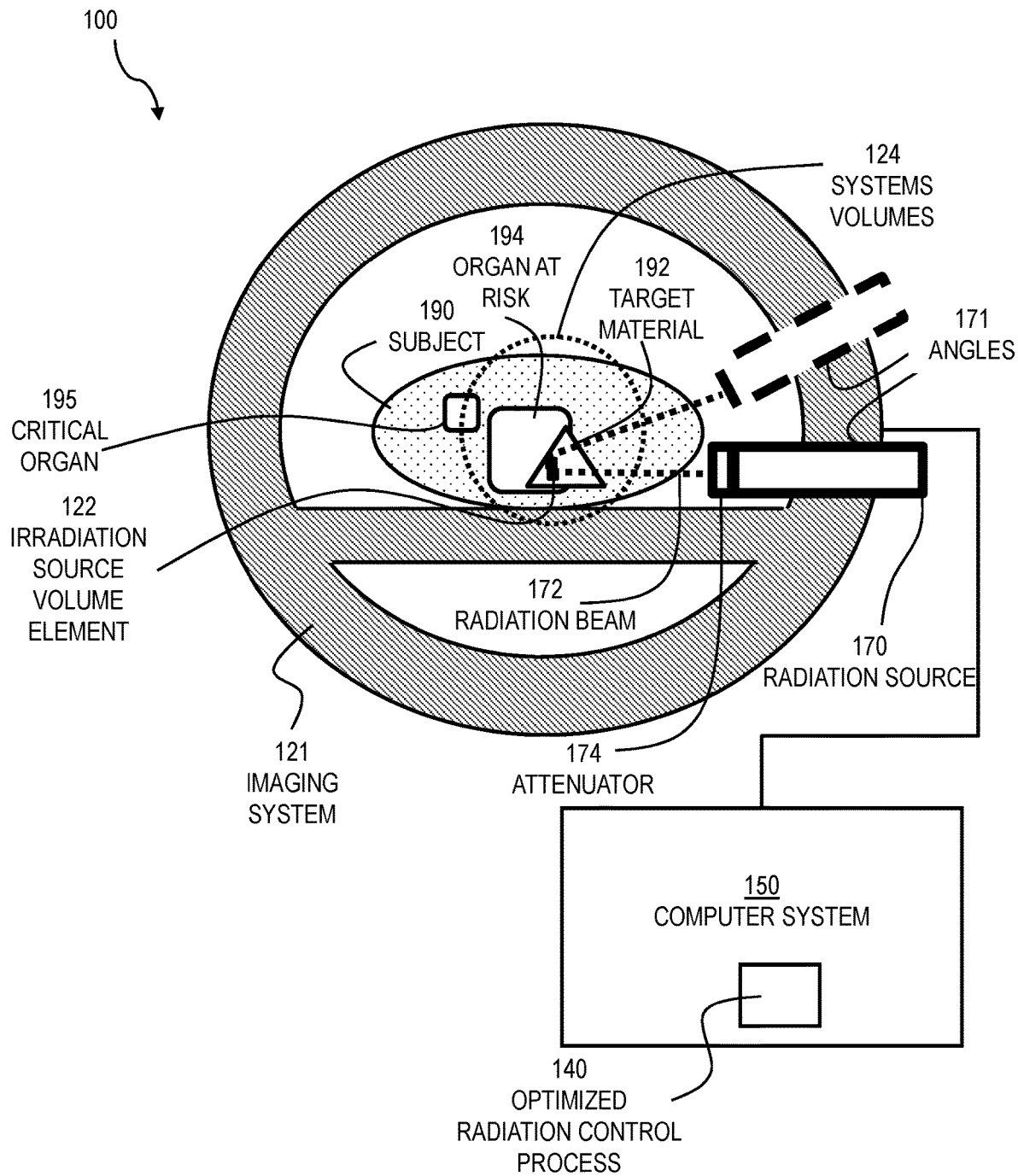
FIG. 1A is a block diagram that illustrates an example system for optimizing a treatment plan for irradiation therapy, according to an embodiment.

FIG. 1A is a block diagram that illustrates an example system 100 for optimizing a treatment plan for irradiation therapy, according to an embodiment. For purposes of illustration, a living subject 190 is depicted, but is not part of the system 100. Zero or more imaging systems 121 are provided, to image the subject 190 within a systems volume 124 that encompasses at least part of the subject 190. In some embodiments, the volume 124 may encompass the entire subject 190. A radiation source 170 is external to the volume 124 and directs radiation into the volume 124 of the subject 190 along one or more tracks. In an example embodiment, the imaging systems 121 obtain measurements that relate to tissue type inside the volume 124. For example, the imaging system 121 is an X-ray Computed tomography (CT) scanner or dual energy CT (DECT) scanner or a nuclear magnetic resonance imagery (MRI) scanner.

As illustrated in FIG. 1A, a target material 192 indicated by a triangle is positioned within the subject 190. In an example embodiment, the target material 192 includes tumor cells. Additionally, an organ-at-risk (OAR) 194 is positioned within the subject 190. Additionally, a critical organ 195 is positioned within the subject 190. The region of the volume 124 that is not occupied by the target material 192, the OAR 194 and the critical organ 195 is occupied by tissues in a category called normal tissue.

As illustrated in FIG. 1A, the system 100 includes a charged particle therapy device including a radiation source 170 that emits a beam 172 that penetrates the volume 124 over a plurality of volume elements or voxels 122 that are defined within a frame of reference of the radiation source 170. In various embodiments, the energy of the beam emitted by the radiation source 170 is controlled, e.g., by controlling the acceleration of the particles or by passing the particles through a removeable constant or variable attenuator 174, or changing a distance from the source to a voxel, or some combination. In some embodiments, the imaging systems 121 define the voxels 122 within the frame of reference of the radiation source 170. The radiation source 170 emits the beam 172 through to the voxels 122 within the volume 124. The beam 172 energy at each voxel 122 is dependent on the emitted energy and the stopping power of the intervening tissues. Combining the effects of multiple beams following different tracks (e.g., directed at different angles 171 as shown in FIG. 1A, or from different translational displacements), the goal is to deliver a high dose within the target material 192 sufficient to damage or kill cells in that target material 192, and a low dose to the normal tissue, the critical organ 195 and the OAR 194.

Figure 7:
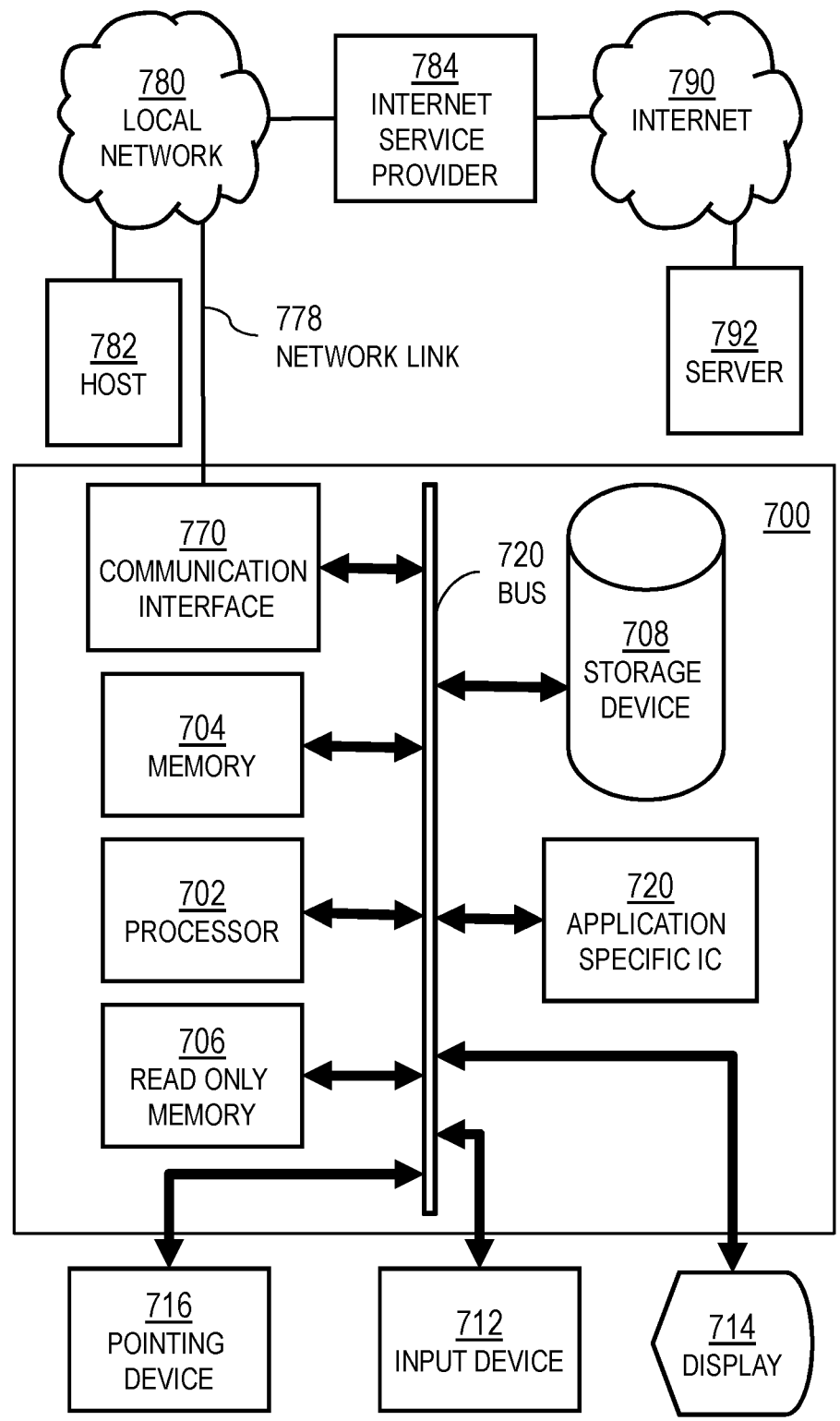
FIG. 7 is a block diagram that illustrates a computer system upon which an embodiment of the invention may be implemented.
Figure 8:
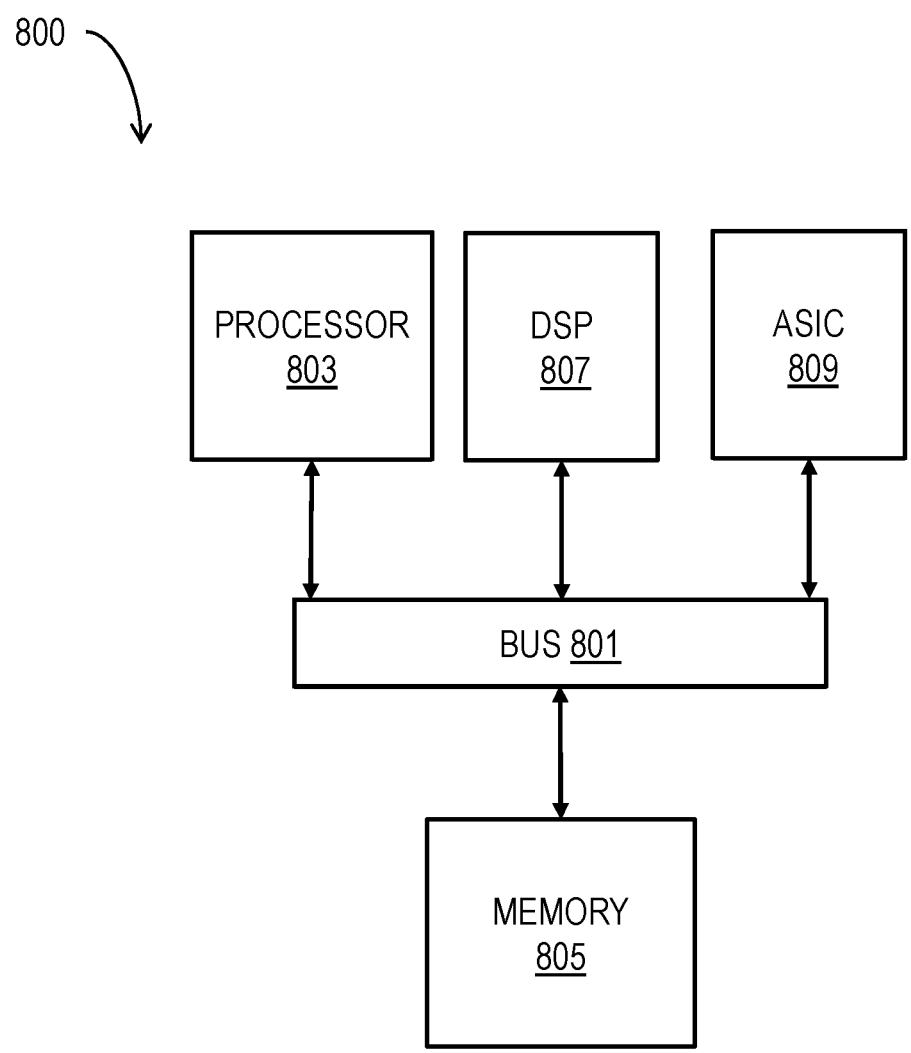
FIG. 8 is a block diagram that illustrates a chip-set upon which an embodiment of the invention may be implemented.

As illustrated in FIG. 1A, a computer system 150 is provided to control the one or more imaging system 121, to collect imaging data from the one or more imaging system 121, or to determine a treatment plan including emitted energy of the radiation source 170 at each track (e.g., angle 171) or to operate the radiation source and any attenuator 174. The computer system 150 includes an optimized radiation control process 140 to perform one or more steps of a method described below with reference to FIG. 4. In various embodiments, the computer system 150 comprises one or more general purpose computer systems, as depicted in FIG. 7 or one or more chip sets as depicted in FIG. 8, and instructions to cause the computer or chip set to perform one or more steps of a method described below with reference to FIG. 4 during or in support of operation of either the imaging system or the radiation device (source 170 and any attenuator 174), or both.

Figure 1B:
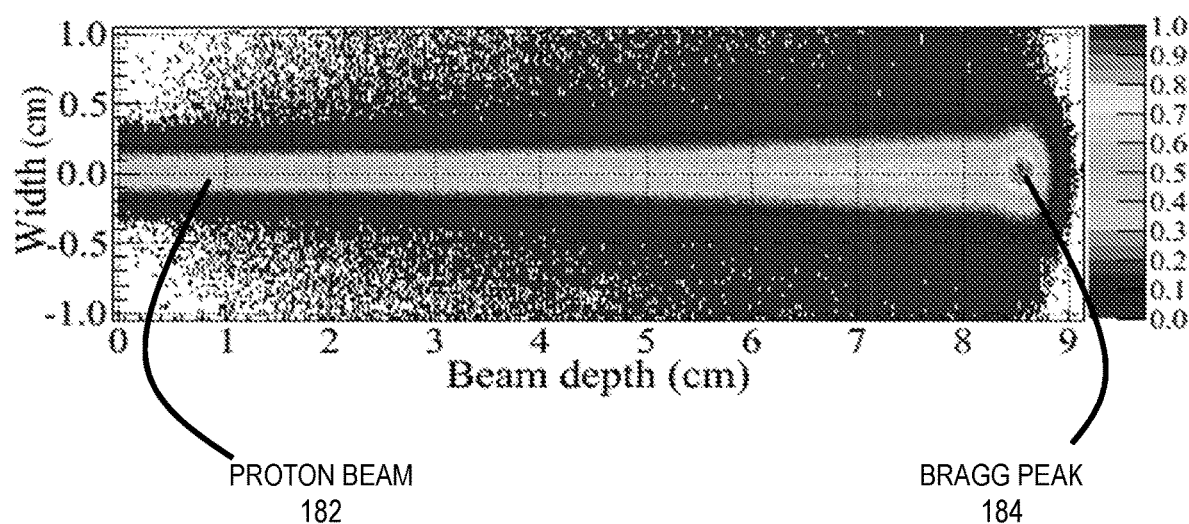
FIG. 1B is a normalized energy dose diagram showing increased charged particle absorption along a ray to a Bragg peak absorption, followed by a steep gradient and little or no absorption, according to an embodiment.

FIG. 1B is a normalized energy dose diagram showing increased proton absorption along a track to a Bragg peak absorption, followed by a steep gradient and little or no absorption, according to an embodiment. The horizontal axis indicates distance in the target volume along the beam track of FIG. 1A and the vertical axis indicates distance in the target volume perpendicular to that track. The proton beam 182 track, and Bragg peak 184 where the most energy is concentrated near 8.5 cm along track, are clearly evident.

Figure 1C:
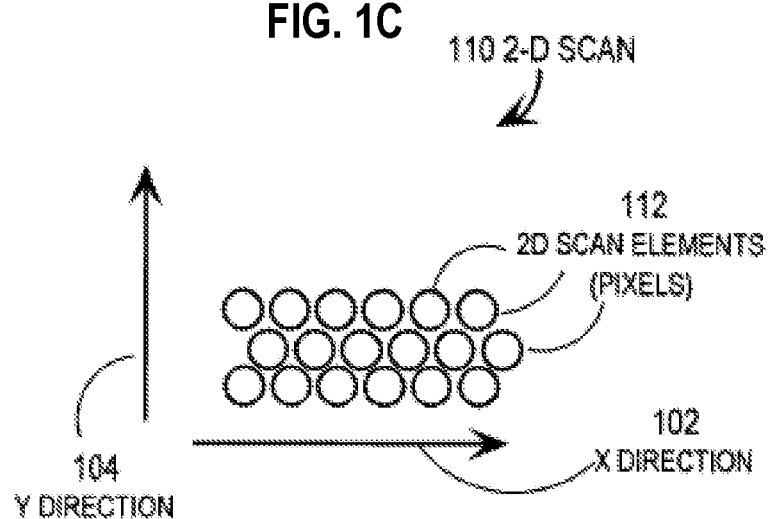
FIG. 1C is a block diagram that illustrates an example of scan elements in a 2D scan, such as one scanned image from a CT or MRI scanner.

FIG. 1C is a block diagram that illustrates scan elements in a 2D scan 110, such as one scanned image of the volume 124 from the imaging system 121, such as a CT or MRI scanner. The two dimensions of the scan 110 are represented by the x direction arrow 102 and the y direction arrow 104. The scan 110 consists of a two-dimensional array of 2D scan elements (pixels) 112 each with an associated position. Typically, a 2D scan element position is given by a row number in the x direction and a column number in the y direction of a rectangular array of scan elements. A value at each scan element position represents a measured or computed intensity or amplitude that represents a physical property (e.g., X-ray absorption, or resonance frequency of an MRI scanner) at a corresponding position in at least a portion of the spatial arrangement of the subject. The measured property is called amplitude hereinafter and is treated as a scalar quantity. In some embodiments, two or more properties are measured together at a pixel location and multiple amplitudes are obtained that can be collected into a vector quantity, such as spectral amplitudes in MRSI or the two absorption values of a DECT. Although a particular number and arrangement of equal sized circular scan elements 112 are shown for purposes of illustration, in other embodiments, more elements in the same or different arrangement with the same or different sizes and shapes are included in a 2D scan.

Figure 1D:
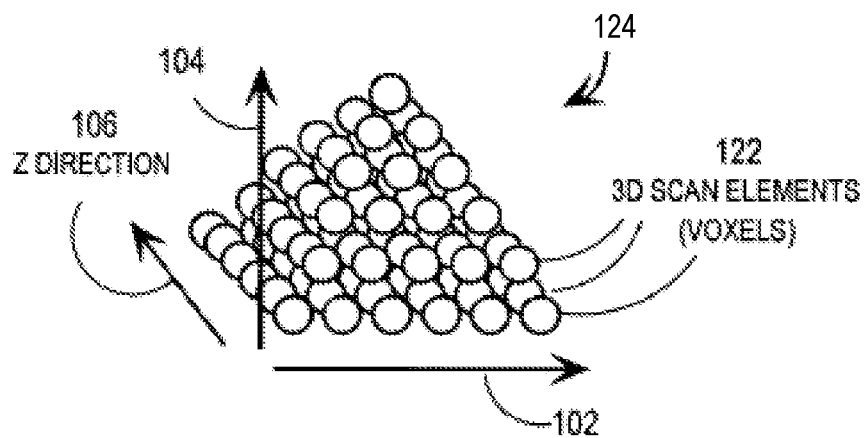
FIG. 1D is a block diagram that illustrates the plurality of voxels 122 that are defined in the volume 124 within a fixed frame of reference of the radiation source 170 of FIG. 1A.

FIG. 1D is a block diagram that illustrates the plurality of voxels 122 that are defined in the volume 124 within a fixed frame of reference of the radiation source 170 of FIG. 1A. A 3D array of voxels is often comprised of multiple 2D arrays of pixels accumulated during a scanning process. Hereinafter, the terms voxels and pixels are used interchangeably. The fixed frame of reference of the radiation source 170 is defined based on the x-direction 102, y-direction 104 and z-direction 106. Thus, in an example embodiment, a particular voxel 122 within the volume 124 in the frame of reference of the radiation source 170 is assigned a unique x-value, y-value and z-value. Although a particular number and arrangement of equal voxels 122 are shown for purposes of illustration, in other embodiments, more voxels 122 in the same or different arrangement with the same or different sizes and shapes are included in the frame of reference of the radiation source 170. In an example embodiment, the voxel 122 has or characterize a sample with a length in a range of 3-5 millimeters, a width in a range of 3-5 millimeters and a depth in a range of 2-3 millimeters.

As previously discussed, some of the voxels 122 are occupied by target material 192, some of the voxels 122 are occupied by OAR material 194, some of the voxels 122 are occupied by critical organ material 195 and the remaining voxels 122 in the volume 124 are occupied by normal tissue material.

Figure 2:
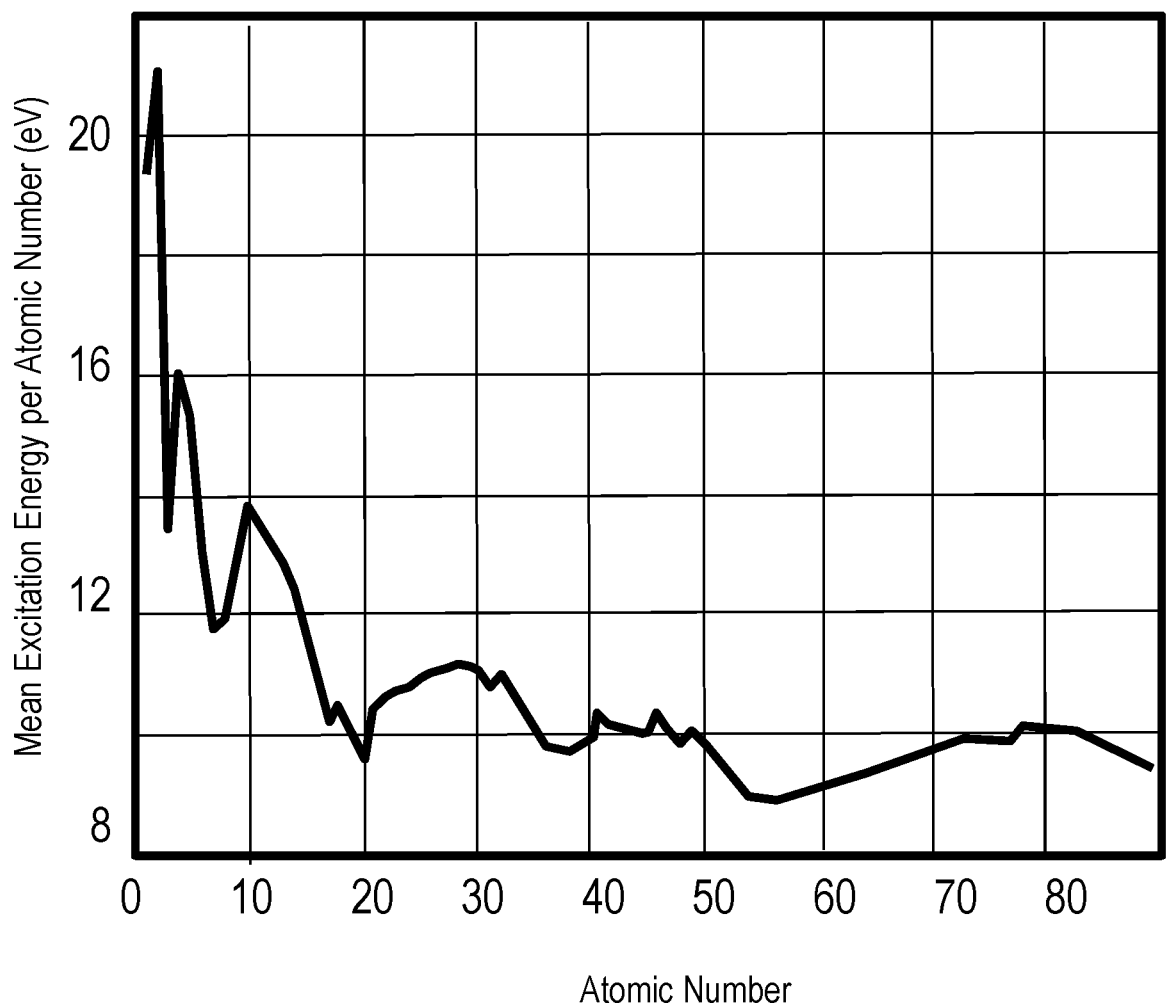
FIG. 2 is a graph that illustrates example mean excitation energy for elements of various atomic numbers, used according to some embodiments.

Fast charged particles, such as protons, moving through matter interact with the electrons of atoms in the material. The interaction excites or ionizes the atoms. This leads to an energy loss of the traveling particle. The Bethe formula describes the mean energy loss per distance travelled of a charged particle (e.g., proton, alpha particle, atomic ion) traversing a material, m—alternatively called the mass stopping power of the material m, and represented by the symbol S/ρ. The stopping power ratio (SPR) is the ratio of the mass stopping power of the material compared to the mass stopping power of water and is represented by the symbol $$\left(\frac{s}{\rho}\right)^m_{water},$$

and given by Equation 1.

$$SPR = \left(\frac{s}{\rho}\right)^m_{water} = \frac{\rho_e^m}{\rho_e^{water}} \times \frac{\ln\left[\frac{2M_e c^2 \beta^2}{I_m(1-\beta^2)}\right] - \beta^2}{\ln\left[\frac{2M_e c^2 \beta^2}{I_{water}(1-\beta^2)}\right] - \beta^2} \quad (1)$$

Where ρ is mass density, $\rho_e$ is electron density, c is the speed of light, β is ratio of particle velocity (v) to the speed of light (c), $M_e$ is electron mass, and $I_m$ is the mean excitation energy of material m, the latter given by Equation 2 for a material m compound composed of N elements.

$$\ln I_m = \frac{\left(\sum_{k=1}^{N} \frac{w_i Z_i}{A_i} \ln I_i\right)}{\left(\sum_{k=1}^{N} \frac{w_i Z_i}{A_i}\right)} \quad (2)$$

Where $w_i$ is the weight fraction of the ith element in the compound, $A_i$ is the atomic weight of the ith element, $Z_i$ is the atomic number of the ith element, and $I_i$ is the mean excitation energy of the ith element. The latter is known for many elements, and given, for example, by FIG. 2. FIG. 2 is a graph that illustrates example mean excitation energy for elements of various atomic numbers. The vertical axis gives $I_m$ in electron volts per atomic number ($Z_m$).

Of the terms in Equation 1, only $\rho_e^m$ and $I_m$ vary with material m along the beam track. Note that $Z_i/A_i$ is close to one for hydrogen and is closer to ½ for other elements because of the presence of neutrons. Note also that $I_m/Z_m$ is also about 50% larger for hydrogen than for other most common components of organic tissue such as Carbon ($Z_c$=6) and Oxygen ($Z_o$=8) which are approximately equal to each other in FIG. 2A. When the y-axis value in the plot of FIG. 2 is multiplied by the corresponding value of $Z_m$, Im is much smaller for hydrogen than for Carbon and Oxygen that have Zm values at least 6 times greater than Hydrogen, but still similar to each other (6 and 8 being only 25% different). Thus, $I_m$ is expected to decrease more with changes in hydrogen than with changes in carbon or oxygen or other, more rare elements in organic tissue. Therefore, SPR is expected to increase more with changes in hydrogen density than with changes in density of other elements. In addition, the electron mass density $\rho_e^m$ of hydrogen is about twice that of other materials because hydrogen lacks neutrons, again leading to an increase in SPR with an increase in hydrogen density.

This expected dependence of SPR on hydrogen density can be exploited by determining a new calibration curve between the two properties using measurements of both hydrogen density and SPR, rather than X-ray absorption in Hounsfield units and SPR. Then, independent measurements or inferences of hydrogen density at each voxel along a track are used with the new calibration curve to deduce a better value for SPR at each voxel. With the better values of SPR, a better range to the Bragg peak can be determined. With the better range to the Bragg peak, a better treatment plan can be devised.

Hydrogen density at a voxel can be determined in a variety of ways. In one approach, magnetic resonance imaging (MRI) is used to detect hydrogen density. Hydrogen density is apparent in a proton density weighted MRI image, which is an image produced by controlling the selection of scan parameters to minimize the effects of relaxation times $T_1$ and $T_2$, resulting in an image dependent primarily on the density of protons in the imaging volume. Longitudinal relaxation ($T_1$) describes the decay of the excited magnetization in the direction of the magnetic field; transverse relaxation ($T_2$) describes the decay of the excited magnetization perpendicular to the applied magnetic field. Proton density contrast is a quantitative summary of the number of protons per unit tissue. The higher the number of protons in a given unit of tissue, the greater the transverse component of magnetization, and the brighter the signal on the proton density contrast image. These protons are hydrogen nuclei, and thus the proton density changes apparent in voxels from MRI give hydrogen density changes in the corresponding voxels directly.

In another approach, hydrogen density is inferred from tissue types, and tissue types are inferred from CT imagery using known segmentation methods. For example, a CT scan is segmented manually or using one or more automated assists or stand-alone automated methods. Each voxel is then characterized as adipose, breast, water, muscle, liver, bone, brain, lung, etc., based on the segmentation method. The hydrogen density associated with each tissue type is then used for any voxel within the segmented area or volume. An advantage to this approach, is that pre-determined values of hydrogen density can be used and there is no need to do time consuming measurements of SPR to develop tables of SPR for dozens or hundreds of tissue types.

In some of these embodiments, an interim determination of hydrogen density is not used. Instead, this expected dependence of SPR on tissue type can be exploited by determining a new calibration entry for each tissue type in a table of SPR values by tissue type. For example, measurements of SPR are made and averaged for each of several tissue types, such as adipose, breast, water, muscle, liver, and bone, or surrogates for same. An advantage of this approach is that reliance on an imperfect relationship between hydrogen density and SPR is avoided. An advantage of the hydrogen density approach is that more-readily available, pre-determined values of hydrogen density can be used and there is no need to do time consuming measurements of SPR to develop tables of SPR for dozens or hundreds of tissue types for which hydrogen density is already known or measured.

FIG. 3A through FIG. 3D are block diagrams that illustrate example measurement equipment used to determine a calibration curve for SPR dependence on hydrogen density, according to an embodiment. In these experiments, plugs of known materials with known hydrogen density were placed in the path of a proton beam. The dose delivered to a plug of known size was measured to deduce the stopping power ratio.

Figures 3A, 3B:
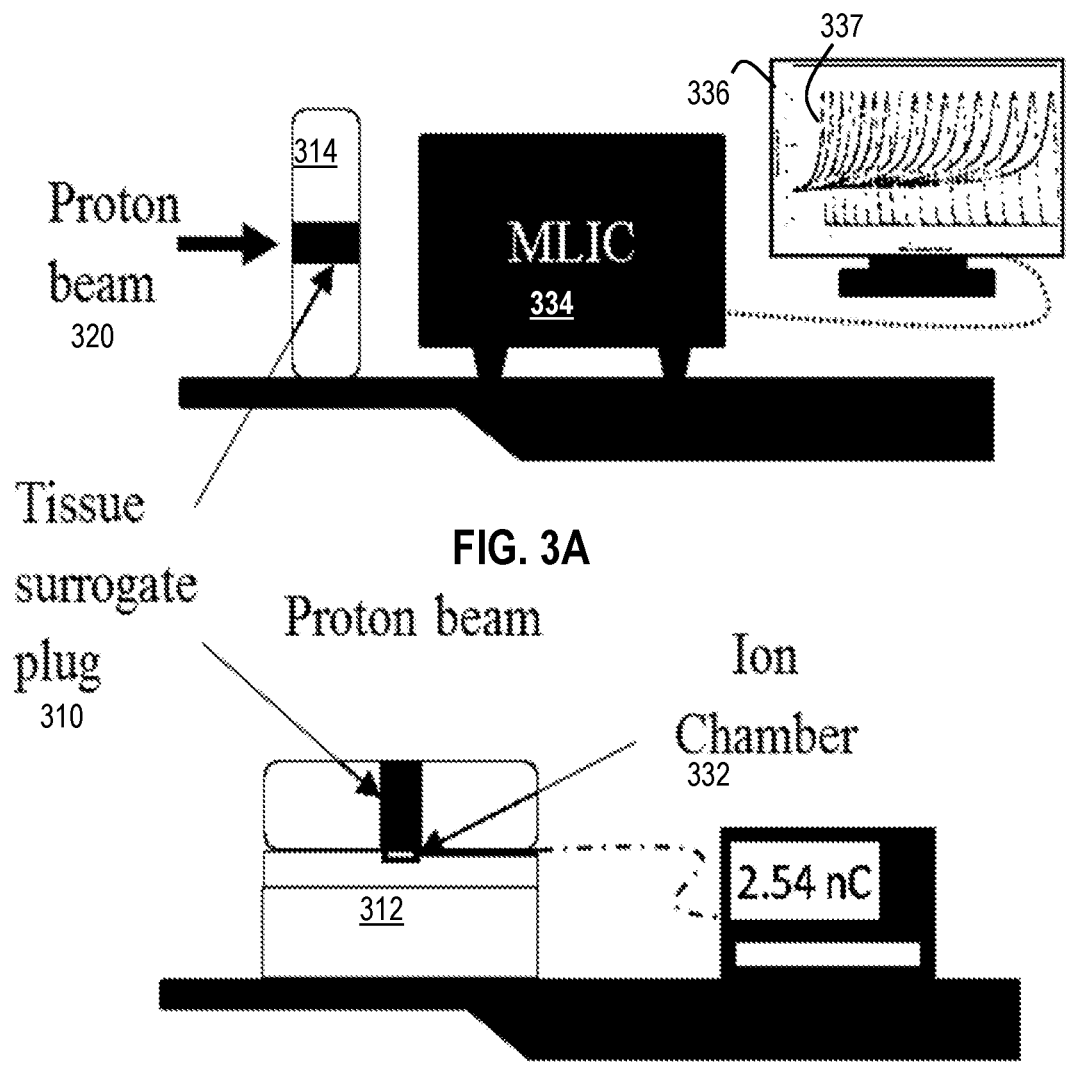

FIG. 3B is a block diagram that illustrates an example ion chamber measurement of dose from a proton beam, to build a new calibration curve, according to an embodiment. An ionization chamber 332 measures charge from ion pairs created within a gas caused by incident charged particles, such as protons or Carbon ions. The chamber is made up of a gas-filled chamber with two electrodes—an anode and a cathode. The electrodes may be in the form of parallel plates (Parallel Plate Ionization Chambers: PPIC), or a cylinder arrangement with a coaxially located internal anode wire. A voltage potential is applied between the electrodes to create an electric field in the fill gas. When gas between the electrodes is ionized by incident beam of charged particles, ion-pairs are created and the resultant positive ions and dissociated electrons move to the electrodes of the opposite polarity under the influence of the electric field. This generates an ionization current which is measured. The accumulated charge from this current is proportional to the number of ion pairs created, and hence proportional to the radiation dose.

In FIG. 3B, a tissue surrogate plug 310 is placed in the path of a proton beam. The plug 310 is supported in a holder 312 that is effectively transparent to the proton beam. In a control measurement, the space of the plug is filled with water. As the dose delivered past the plug into the ion chamber is diminished by the introduction of the plug 310 of known length in the path of the proton beam, compared to the diminished dose when water is inserted in the same space, the stopping power ratio is determined. In the illustrated embodiment, the dose measured is based on an accumulated charge of 2.54 nanoCoulombs (nC, 1 nC=$10^{-9}$ Coulombs).

FIG. 3A is a block diagram that illustrates an example multilayer ionization chamber (MLIC) measurement of dose from a proton beam to build a new calibration curve, according to an embodiment. In FIG. 3A, a proton beam 320 is directed onto a plug 310 of water or tissue or tissue surrogate. The plug 310 is supported in a holder 314 that is effectively transparent to the proton beam. A multilayer ion chamber 334 records the dose deposited into each ion chamber of several layered ion chambers. The result is a dose versus layer plot, which can show the Bragg peak in one of the deeper layers, as indicated by the traces 337 on a monitor 336. In a control measurement, the space of the plug is filled with water. As the dose is diminished by the introduction of the plug 310 of known length in the path of the proton beam, compared to the diminished dose when water is inserted in the same space, the stopping power ratio is determined.

FIG. 3C is a block diagram that illustrates an example ionization chamber measurement of dose from a proton beam to build a new calibration curve, according to an embodiment. In FIG. 3C, a proton beam (not shown) is directed downward onto a plug that is 4.51 centimeters (cm, 1 cm=$10^{-2}$ meters) long. FIG. 3C demonstrates a cross-sectional dose distribution in the phantom, which is often acquired from a commercially available Radiation Treatment Planning System (RTPS) which enables one to simulate the proton induced dose distributions in the material. The plug material is water or tissue or tissue surrogate. The plug 340 is supported in a holder 344 that is effectively transparent to the proton beam. An ion chamber 334 records the dose deposited into each two-dimensional bin of the measurement device. FIG. 3D is a zoomed view of FIG. 3C. Based on the change of dose through the plug, the 4.51 cm of material depicted has the same stopping power as 5.02 centimeters of water (also called the water equivalent depth, WED). The SPR is thus 5.02/4.51=1.113.

Figure 3E:
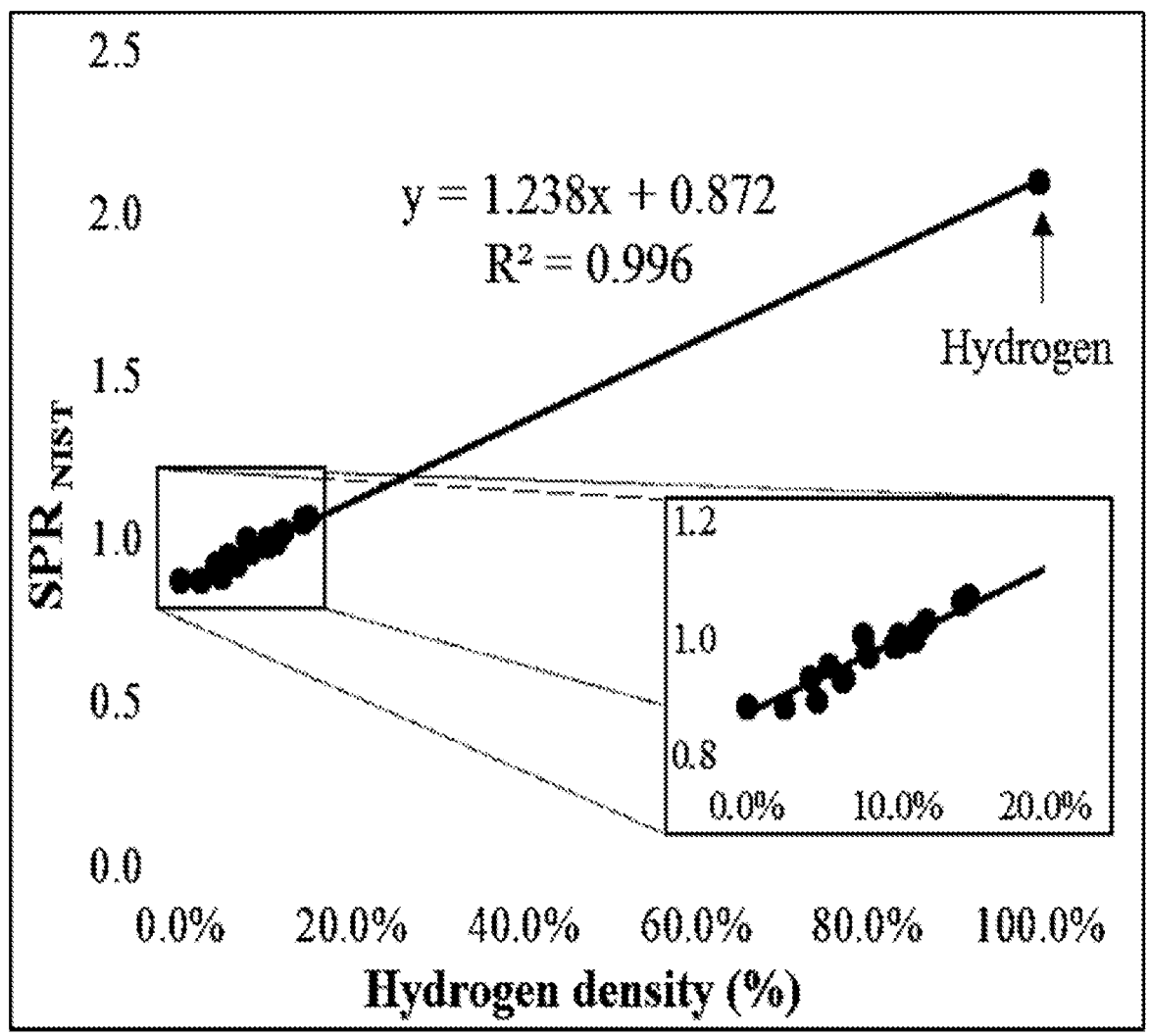
FIG. 3E is a graph that illustrates an example calibration curve for the relationship between SPR and hydrogen density in various tissues, according to an embodiment.

Samples of 22 materials with known SPR were used from the National Institute of Standards and Technology (NIST) databases to investigate correlations between SPR and hydrogen density correlation. Hydrogen density was calculated based on the known molecular makeup of the various materials. Note that such a correlation is a measured approximation due to the equipment used and not a natural law for which a relationship is exact regardless of any measurement device. FIG. 3E is a graph that illustrates an example calibration curve for the relationship between SPR and hydrogen density in various tissues, according to an embodiment. The value for pure hydrogen is obtained, as well as the values measured for the other NIST materials that all had hydrogen densities in a range from zero to about 20%. These points can be fit with any mathematical model, such as a polynomial or exponential fit. In the illustrated embodiment, a linear fit was deemed suitable, with an $R^2$ value of 0.996. The linear fit, new calibration curve is given by Equation 3a.

$$SPR=0.872+1.238*HD \qquad (3a)$$

Where HD is hydrogen density in percent. Considering the measurement uncertainties of both HD and SPR, variations in the coefficients of Equation 3a are used in some embodiments, as expressed in Equation 3b.

$$SPR=0.872(\pm 0.1)+1.238(\pm 0.2)*HD \qquad (3b)$$

In other embodiments, other materials with other hydrogen densities are measured or other sensors used and fit with the same or different order polynomial with similar or different coefficients and adding one or more different independent variables. In some embodiments, measurements of SPR and hydrogen density are made, and mathematical models are fit for other subjects—such as other animals or plants or manufactured items.

Figure 4:
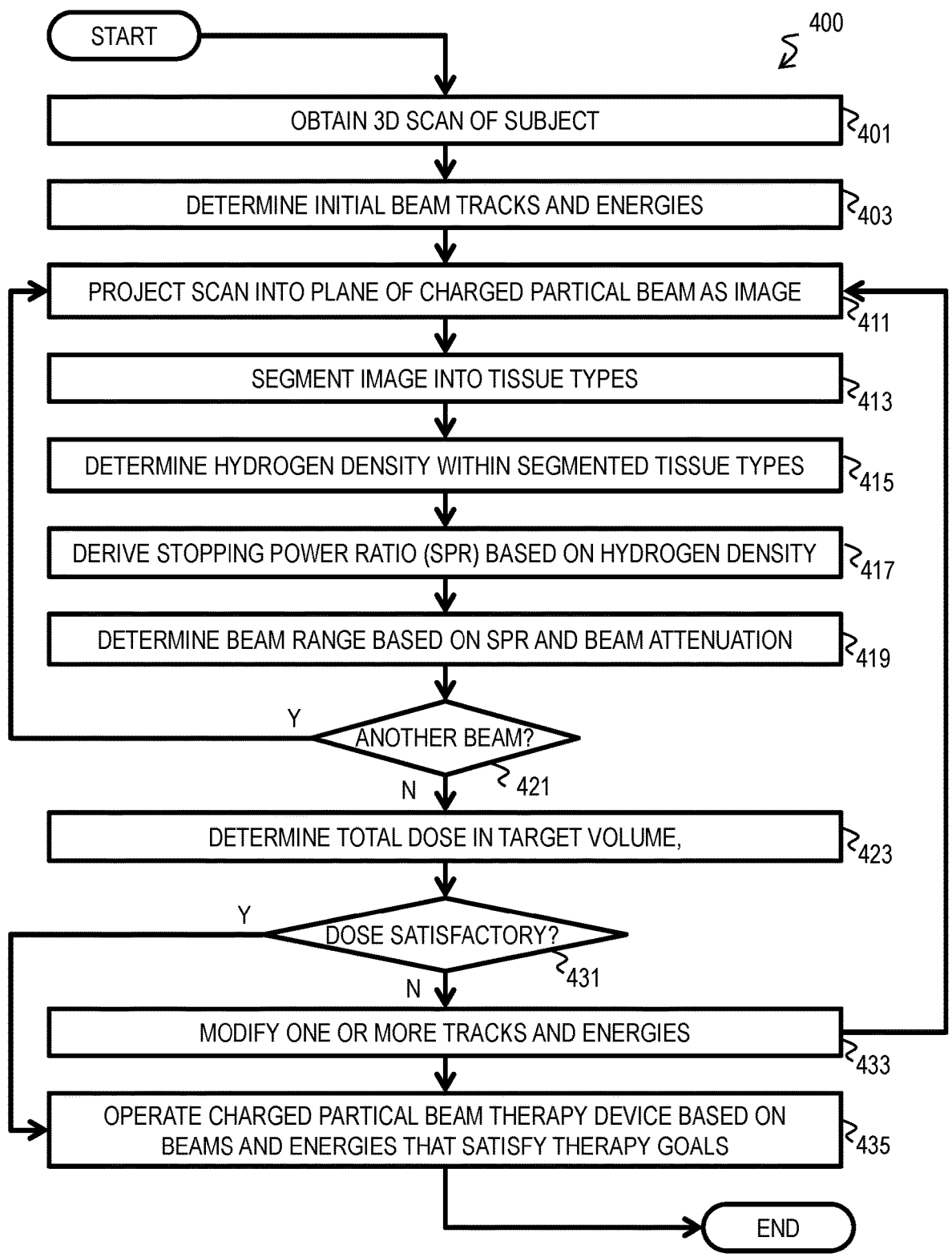
FIG. 4 is a flow diagram that illustrates an example method for optimizing a treatment plan for irradiation therapy using hydrogen density, according to an embodiment.

FIG. 4 is a flow diagram that illustrates an example method 400 for optimizing a treatment plan for irradiation therapy using hydrogen density, according to an embodiment. Although steps are shown in FIG. 4 as integral blocks in a particular order, in other embodiments, one or more steps or portions thereof are performed in a different order or overlapping in time, in series or in parallel, or are omitted or one more additional steps are added.

In step 401, a 3D scan is made of a subject to be treated with a charged particle beam. In some embodiments the 3D scan is made with an instrument that directly detects hydrogen density variations, such as an MRI operated for one or more proton density weighted MRI images. In other embodiments, the 3D scan is made in another way that allows an inference of tissue type within segmented regions of the 3D scan, such an MRI device operated in a different mode such as spectral imaging mode, or CT imagery, or DECT imagery or ultrasound imagery. In some embodiments, step 401 includes segmenting the 3D scan into regions of a single category of tissue type. For example, in some such embodiments, step 401 includes segmenting, into tissue type categories, 3D scans that do not directly detect hydrogen density variations. Thus, in some embodiments, step 401 includes segmenting the medical image data into a tissue type at each voxel based on absorption value at each voxel and location inside patient of each voxel.

Figure 5:
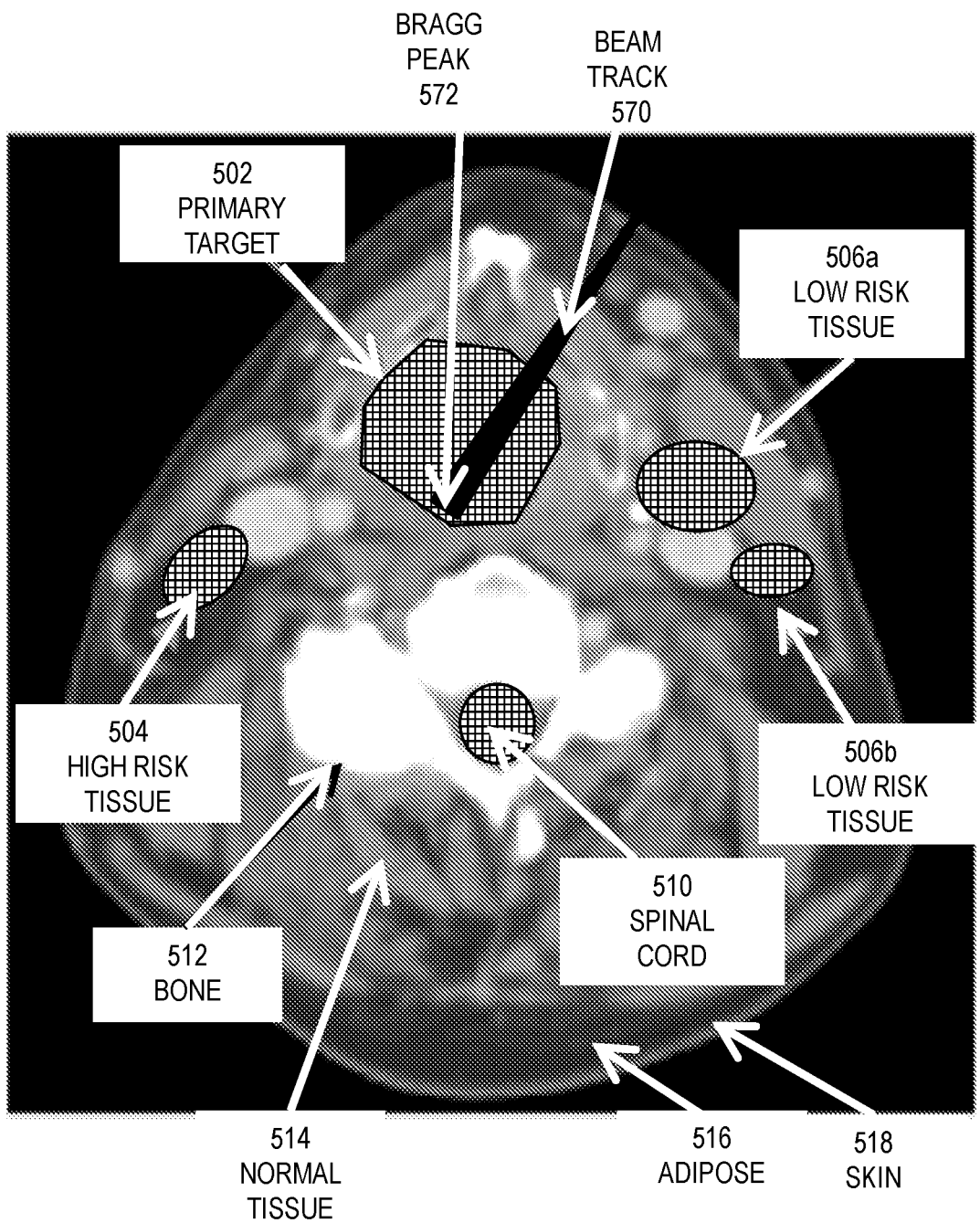
FIG. 5 is a block diagram that illustrates an example solution to the placement of a Bragg peak in the head and neck of a subject during a treatment plan optimization method, according to an embodiment.

FIG. 5 is a block diagram that illustrates an example solution to the placement of a Bragg peak in a subject during a treatment plan optimization method, according to an embodiment. This example is based on having a 3D CT scan that does not give voxel values that indicate hydrogen density variations directly. Based on the CT scan, different tissue types are evident and segmented. For purpose of illustration, it is assumed that each voxel is assigned to one of these tissue types: primary target tissue 502, e.g., tumor; high risk tissue 504 near the target tissue, e.g., gland; low risk tissue 506a and 506b, near the target tissue but less vulnerable to a particular dose than high risk tissue 504, e.g., lymph nodes; spinal cord tissue 510; bone 512, normal tissue 514, e.g., connective tissue; adipose tissue 516; and skin 518. For purpose of illustration, it is assumed that each different tissue type has an associated hydrogen density value.

Returning to FIG. 4, in step 403 an initial treatment plan is devised based on any known method to determine initial tracks and initial emitted energies for each track, e.g., using the HU stoichiometric calibration curve. For example, in FIG. 5, first beam track 570 is proposed in an initial treatment plan with an expected Bragg peak 572 within the primary target tissue 502.

Returning to FIG. 4, in step 411, for each track in the initial plan, the 3D scan is projected into one or more scan planes that each includes, as closely as efficient with the available technology, the longitudinal axis of the current track. In step 413, the projected scan plane is segmented into areas of a single category of tissue type. For example, in some such embodiments, step 413 includes segmenting into tissue type categories, a projected scan plane for a scan that does not directly detect hydrogen density variations. If the 3D scan was already segmented in step 403 or the 3D scan gives hydrogen density variations per voxel directly, then, in some embodiments, step 413 is omitted. The advantage of segmenting in step 413 instead of step 403, is that a smaller number of voxels need to be segmented. Thus step 413 includes segmenting the medical image data into a tissue type at each voxel based on absorption value at each voxel and location inside patient of each voxel for at least each voxel along the first beam. An advantage of segmenting in step 403 instead of step 413, is that segmenting can be done once for the subject and reused as different projected planes intersect similar or close regions of the 3D scan.

In step 415, the hydrogen density is determined for voxels in the current track. Thus step 415 includes, for a first beam having a first track and first emitted energy, determining hydrogen density at each voxel along the first beam selected from the plurality of voxels based on the medical image data. In some embodiments, step 415 is based on the proton density MRI image and is either trivial, or omitted as already accomplished in step 411. However, in some embodiments in which the projected scan plane does not give hydrogen density variations directly, step 415 is based on the areas of the segmented tissue type. Thus, in such embodiments, step 415 includes determining hydrogen density at each voxel based on tissue type at each voxel for at least each voxel along the first beam.

In step 417, stopping power ratio (SPR) is derived based on the hydrogen density at each voxel. Thus, step 417 includes deriving stopping power ratio along the first beam based on the hydrogen density at each voxel along the first beam selected from the plurality of voxels. In some embodiments, this is done by evaluating Equation 1 at each voxel for a material m based on tissue type. In some of these embodiments, the non-hydrogen makeup of tissue types are held constant except for hydrogen percentage by weight ($w_H$). In other embodiments, this is accomplished using the measured or inferred hydrogen density and a calibration curve based on SPR measurements and hydrogen density of various materials with different hydrogen densities, such as the calibration curve of FIG. 3E, e.g., as given by Equation 3. Thus, step 417 includes calculating stopping power ratio along the first beam based on the hydrogen density at each voxel along the first beam selected from the plurality of voxels. The advantage of using a calibration curve based on SPR measurements, like Equation 3, is that the computation is much faster and less subject to uncertainties in the weight percentages of various elements.

In step 419, the distance range to the Bragg peak along the track for the given initial beam energy (also called "beam range" herein for convenience) is determined based on the SPR at each voxel along the track. In some embodiments the emitted energy is based on a constant energy beam source and a variable beam attenuation provided by an attenuator 174. Thus step 417 includes calculating range to a Bragg peak along the first beam based on the stopping power ratio and the first emitted energy.

In step 421 it is determined whether there is another beam. If so, control passes back to step 411 to repeat the loop of steps 411 through step 421 for the next beam of the plurality of beams in the current plan, which in the first execution of step 421 in time is the initial plan of step 403. If all the beams have had beam range determined, then control passes to step 423.

In step 423, the total dose within the voxels of the target volume is determined, by summing the deposited dose at each voxel based, at least in part, on the beam range for each beam in the current plan. In step 431, it is determined whether the total dose deposited in the target volume is satisfactory, e.g., is sufficient to deliver the treatment dose to the target tissue in all voxels associated with the target tissue. In some embodiments, step 431 includes determining that several previous attempts have not improved the agreement with the target dose. If so, the treatment plan is considered to be optimal in some way, and control passes to step 435, described below. If not, control passes to step 433.

In step 433, one or more beam tracks or emitted energies or both are modified based on the dose difference detected in step 423 and the beam range determined in step 419. Thus step 433 includes modifying the first beam track or the first emitted energy of the first beam, or both, based at least in part on the range to the Bragg peak to determine a second track and second emitted energy of a modified beam. Any method to perform the modification can be used. For example, given a previous modification result, a new modification can be recommended by using the observed rate of change of the result to estimate a new value that is expected to provide a result closer to the treatment target dose. A straight extrapolation or a genetic random extrapolation can be used, for example, in various embodiments. In some embodiments, Multi-Criteria Optimization (MCO) is used, as described in Van de Water et al., Long et al. and Craft et al. (see References section). Control then passes back to step 411 to repeat the loop of steps from 411 to 433 for the modified treatment plan as the current treatment plan.

If it is determined in step 431, that the dose is satisfactory, and thus the treatment plan is optimal, then in step 435, the modified beam tracks and corresponding source energies are used to deliver treatment. This can be done by operating the radiation treatment equipment or by outputting data that indicates the optimized treatment plan, with one or more tracks or emitted energies modified based on the new beam range, e.g., by presenting on a display or sending a message with output data. Thus, step 435 includes causing the radiation source to be operated to deliver the modified beam by sending output data that indicates the second track and second emitted energy of the modified beam.

Thus, method 400 improves measurement of tissue SPR by including measurement of hydrogen density to reduce range uncertainty in particle delivery, such as in radiotherapy treatments. Thus, the method implements hydrogen density information into a model or calculation algorithm. The method can substantially reduce the need for additional and expensive tools, such as Dual Energy CT (DECT)

2. Example Embodiments

The method 400 using calibration curve of Equation 3 based on the data of FIG. 3E was tested with computed and measured values of SPR. In one embodiment, the method considers hydrogen density of a material to calculate the CPB dose in order to reduce range uncertainty. For example, one embodiment of the method can reduce range uncertainty from the range of 2.7% to 3.5% using typical methods that rely heavily on distribution of the electron density rather than hydrogen density, to approximately less than 2% uncertainty.

In this example embodiment, Equation 3 based on the data of FIG. 3E was used to calculate SPR based on predetermined hydrogen density associated with various tissue types and phantom materials listed by NIST. That value of SPR was used to calculate other measures of charge particle beam ranges, such as water equivalent depth (WED), and dose. The dose is the average energy transferred per unit mass. The dose is distributed unevenly along the protons' path, with most of it transferred at the end of the track at the Bragg peak, as illustrated in FIG. 1B. In addition, in this embodiment, the actual SPR was measured as described above in text associated with FIG. 3A through FIG. 3D. The measured SPR was used to determine a measured value of WED and dose was measured in an ion chamber, as depicted in FIG. 3B. The difference between measured and calculated values were expressed as a percentage and graphed in FIG. 6.

Figure 6:
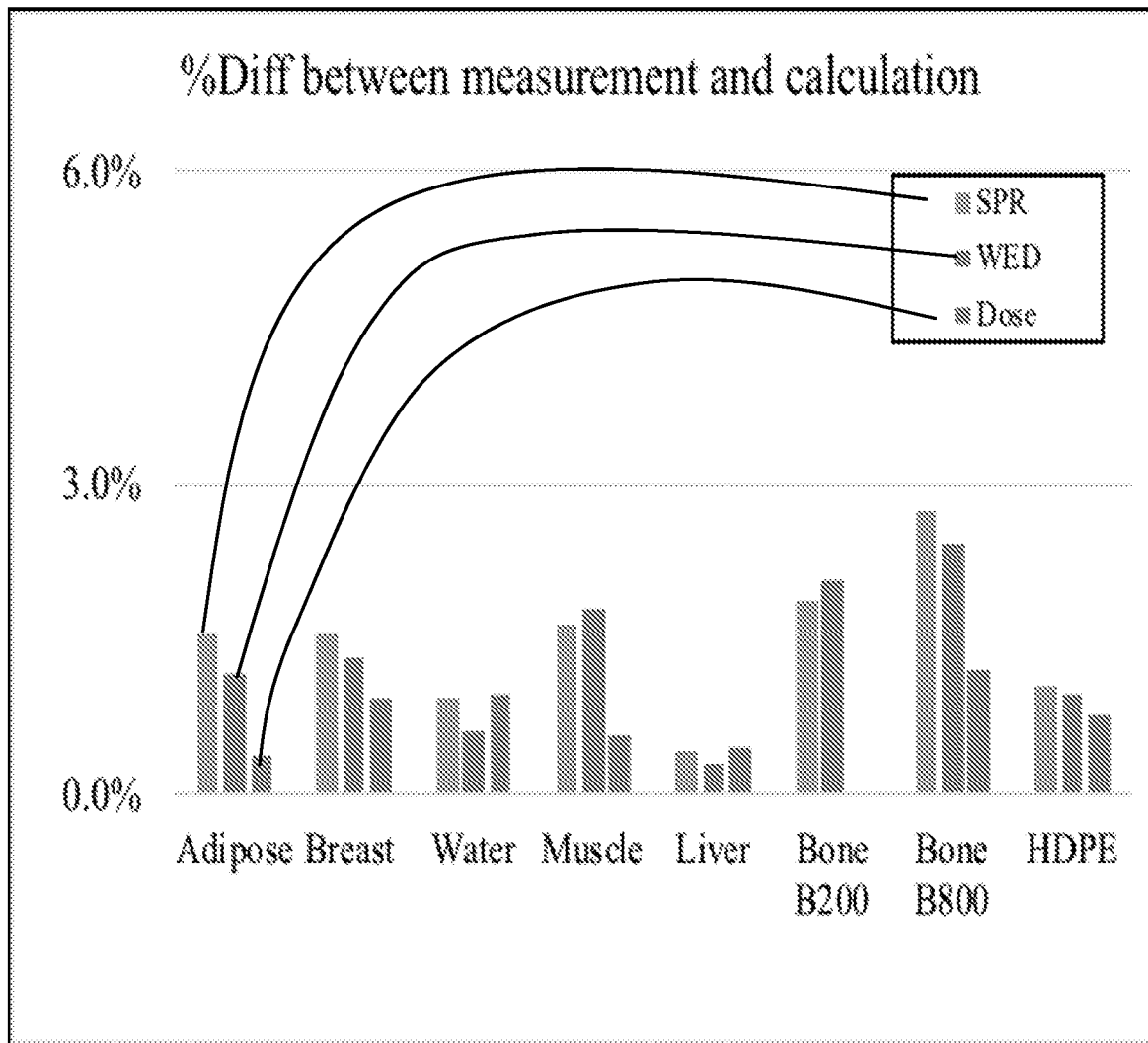
FIG. 6 is a graph that illustrates the improvement in the calculation of proton absorption during optimization of a treatment plan, according to an embodiment.

FIG. 6 is a graph that illustrates the improvement in the calculation of proton absorption during optimization of a treatment plan, according to an embodiment. The vertical axis indicates percent difference between measured and calculated values. The horizontal axis indicates eight different tissues/materials available as plugs 310 for measurements. The eight types of tissue/materials are, in the order of FIG. 6: Adipose, breast, water, muscle, liver, bone phantom B200, bone phantom B800, and high density polyethylene (HDPE). For each material, there are three bars, the first for SPR, the second for WED and the third for dose. FIG. 6 shows that the percent difference in every case is less than 3.5%, and thus superior to the errors using the Hounsfield units stochiometric calibration curve of the prior art. Indeed, the error is typically about 2% or less.

As a result, the method 400 can provide a more accurate SPR prediction of different materials in the particle beam path as the beam traverses a subject and less uncertainty in the dose distribution. Thus, the method can reduce range uncertainty of particle delivery to improve treatment planning and patient outcome.

3. Computational Hardware Overview

FIG. 7 is a block diagram that illustrates a computer system 700 upon which an embodiment of the invention may be implemented. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 700, or a portion thereof, constitutes a means for performing one or more steps of one or more methods described herein.

A sequence of binary digits constitutes digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitutes computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 770 sends and receives electrical, acoustic or electromagnetic signals, including infrared and optical signals, that carry information streams, such as digital data.

The term computer-readable medium is used herein to refer to any medium that participates in providing information to processor 702, including instructions for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 702, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 702, except for carrier waves and other signals.

Logic encoded in one or more tangible media includes one or both of processor instructions on a computer-readable storage media and special purpose hardware, such as ASIC 720.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software.

The signals transmitted over network link 778 and other networks through communications interface 770, carry information to and from computer system 700. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a signal on a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to a signal on an infra-red a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

FIG. 8 illustrates a chip set 800 upon which an embodiment of the invention may be implemented. Chip set 800 is programmed to perform one or more steps of a method described herein and includes, for instance, the processor and memory components described with respect to FIG. 7 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 800, or a portion thereof, constitutes a means for performing one or more steps of a method described herein.

In one embodiment, the chip set 800 includes a communication mechanism such as a bus 801 for passing information among the components of the chip set 800. A processor 803 has connectivity to the bus 801 to execute instructions and process information stored in, for example, a memory 805. The processor 803 may include one or more processing cores with each core configured to perform independently. A multi-core processor enables multiprocessing within a single physical package. Examples of a multi-core processor include two, four, eight, or greater numbers of processing cores. Alternatively or in addition, the processor 803 may include one or more microprocessors configured in tandem via the bus 801 to enable independent execution of instructions, pipelining, and multithreading. The processor 803 may also be accompanied with one or more specialized components to perform certain processing functions and tasks such as one or more digital signal processors (DSP) 807, or one or more application-specific integrated circuits (ASIC) 809. A DSP 807 typically is configured to process real-world signals (e.g., sound) in real time independently of the processor 803. Similarly, an ASIC 809 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 803 and accompanying components have connectivity to the memory 805 via the bus 801. The memory 805 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 805 also stores the data associated with or generated by the execution of one or more steps of the methods described herein.

4. Alternative, Extensions and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

5. References

The following references expand details on the various statements made herein.

Bar et al, "Experimental validation of DECT for proton therapy using heterogeneous tissue samples", Med. Phys. 45 (1), 2018.

Craft D, Richter C. Deliverable navigation for multicriteria step and shoot IMRT treatment planning. Phys Med Biol 2013; 58: 87-103.

Li et al, "Comprehensive analysis of proton range uncertainties related to SPR estimation using dual energy CT imaging", Phys. Med. Biol. 627056, 2017.

Long T, Matuszak M, Feng M, Fraass B A, Ten Haken R K, Romeijn H E. Sensitivity analysis for lexicographic ordering in radiation therapy treatment planning. Med Phys 2012; 39: 3445-55.

Mohler et al, "Methodological accuracy of image-based electron density assessment using dual-energy computed tomography" Med. Phys. 44 (6), 2017

Paganetti H. Range uncertainties in proton therapy and the role of Monte Carlo simulations. Phys Med Biol 2012; 57: R99-117.

Schneider U, Pedroni E, Lomax A. The calibration of CT Hounsfield units for radiotherapy treatment planning. Phys Med Biol 1996, 41(1):111-24.

Sudhyadhom, "Determination of mean ionization potential using magnetic resonance imaging for the reduction of proton beam range uncertainties: theory and application", Phys. Med. Biol. 62852, 2017

Taasti et al, "Validation of proton stopping power ratio estimation based on dual energy CT using fresh tissue samples" Phys. Med. Biol 14; 63(1):015012. 2017.

Van de Water S, Kraan A C, Breedveld S, Schillemans W, Teguh N, Kooy H M, et al. Improved efficiency of multi-criteria IMPT treatment planning using iterative resampling of randomly placed pencil beams. Phys Med Biol 2013; 58: 6969-83.

Vilches-Frexias et al, "Comparison of projection- and image-based methods for proton stopping power estimation using dual energy CT", Physics and Imaging in Radiation Oncology 328-36, 2017.

Wohlfahrt et al, "Evaluation of Stopping-Power Prediction by Dual- and Single-Energy CT in an Anthropomorphic Ground-Truth Phantom", Int J Radiation Oncol Biol Phys, Vol. 100, No. 1, pp. 244e253, 2018

What is claimed is:

1. A method for charged particle therapy comprising:
obtaining medical image data for a plurality of voxels inside a subject in a reference frame of a radiation source that emits a beam of charged particles in each of a plurality of tracks with a controlled emitted energy at each track;
for a first beam having a first track and first emitted energy, determining hydrogen density at each voxel along the first beam selected from the plurality of voxels based on the medical image data;
calculating automatically on a processor stopping power ratio along the first beam based on the hydrogen density at each voxel along the first beam selected from the plurality of voxels;
calculating automatically on the processor range to a Bragg peak along the first beam based on the stopping power ratio and the first emitted energy;
modifying automatically on the processor the first beam track or the first emitted energy of the first beam, or both, based at least in part on the range to the Bragg peak to determine a second track and second emitted energy of a modified beam; and
causing the radiation source to be operated to deliver the modified beam by sending automatically from the processor output data that indicates the second track and second emitted energy of the modified beam.

2. A method as recited in claim 1, wherein:
the medical image data is proton density data from a magnetic resonance imaging device; and
said determining hydrogen density is performed automatically on a processor.

3. A method as recited in claim 1, wherein:
the medical image data is X-ray absorption data from a computed tomography imaging device; and
said determining hydrogen density further comprises
segmenting the medical image data into a tissue type at each voxel based on absorption value at each voxel and location inside patient of each voxel for at least each voxel along the first beam; and
determining automatically on the processor hydrogen density at each voxel based on tissue type at each voxel for at least each voxel along the first beam.

4. A method as recited in claim 1, wherein:
the medical image data is difference in X-ray absorption data from a dual energy computed tomography (DECT) imaging device; and
said determining hydrogen density further comprises
segmenting the medical image data automatically on a processor into a tissue type at each voxel based on difference value at each voxel for at least each voxel along the first beam; and
determining automatically on the processor hydrogen density at each voxel based on tissue type at each voxel for at least each voxel along the first beam.

5. A method as recited in claim 1, wherein said calculating automatically on a processor stopping power ratio further comprises calculating stopping power ratio as a polynomial function the hydrogen density expressed as a percentage at each voxel along the first beam selected from the plurality of voxels.

6. A method as recited in claim 5, wherein the polynomial function is a linear function for which the stopping power ratio is equal to a constant multiplied by the hydrogen density expressed as a percentage in a percentage range from 0 percent to about 20 percent.

7. A method as recited in claim 6, wherein the linear function gives the stopping power ratio as 0.872 (±0.1) plus 1.238 (±0.2) multiplied the hydrogen density expressed as a percentage.

8. A non-transitory computer-readable medium carrying one or more sequences of instructions, wherein execution of the one or more sequences of instructions by one or more processors causes the one or more processors to perform the steps of:
obtaining medical image data for a plurality of voxels inside a subject in a reference frame of a radiation source that emits a beam of charged particles at a plurality of tracks with a controlled emitted energy at each track;
for a first beam having a first track and first emitted energy, determining hydrogen density at each voxel along the first beam selected from the plurality of voxels based on the medical image data;
calculating stopping power ratio along the first beam based on the hydrogen density at each voxel along the first beam selected from the plurality of voxels;
calculating range to a Bragg peak along the first beam based on the stopping power ratio and the first emitted energy;
modifying the first beam track or the first emitted energy of the first beam, or both, based at least in part on the range to the Bragg peak to determine a second track and second emitted energy of a modified beam; and
causing the radiation source to be operated to deliver the modified beam by sending output data that indicates the second track and second emitted energy of the modified beam.

9. A system comprising:
radiation source that emits a beam of charged particles at a plurality of tracks with a controlled emitted energy at each track;
at least one processor; and
at least one memory including one or more sequence of instructions;
the at least one memory and the one or more sequence of instructions configured to, with the at least one processor, cause the at least one processor to:
obtain medical image data for a plurality of voxels inside a subject in a reference frame of a radiation source that emits a beam of charged particles at a plurality of tracks with a controlled emitted energy at each track;
for a first beam having a first track and first emitted energy, determine hydrogen density at each voxel along the first beam selected from the plurality of voxels based on the medical image data;
calculate stopping power ratio along the first beam based on the hydrogen density at each voxel along the first beam selected from the plurality of voxels;
calculate range to a Bragg peak along the first beam based on the stopping power ratio and the first emitted energy;
modify the first beam track or the first emitted energy of the first beam, or both, based at least in part on the range to the Bragg peak to determine a second track and second emitted energy of a modified beam; and
cause the radiation source to be operated to deliver the modified beam by sending automatically from the processor output data that indicates the second track and second emitted energy of the modified beam.

* * * * *